United States Patent [19]
LaFontaine et al.

[11] Patent Number: 6,035,856
[45] Date of Patent: Mar. 14, 2000

[54] PERCUTANEOUS BYPASS WITH BRANCHING VESSEL

[75] Inventors: Daniel M. LaFontaine, Plymouth; Roger N. Hastings, Maple Grove; Charles L. Euteneuer, St. Michael; Lixiao Wang, Maple Grove, all of Minn.

[73] Assignee: SCIMED Life Systems, Maple Grove, Minn.

[21] Appl. No.: 08/813,040

[22] Filed: Mar. 6, 1997

[51] Int. Cl.[7] .................................................. A61B 19/00
[52] U.S. Cl. ................................ 128/898; 623/1; 623/12
[58] Field of Search ............................... 128/898; 623/1, 623/12, 66, 11, 3; 604/8, 9, 7

[56] References Cited

U.S. PATENT DOCUMENTS

Re. 35,352  10/1996  Peters .
Re. 35,459   2/1997  Junkman .

(List continued on next page.)

FOREIGN PATENT DOCUMENTS

| | | |
|---|---|---|
| 0 769 272 A1 | 4/1997 | European Pat. Off. . |
| 97-281410 | 7/1997 | Japan . |
| 308752 | 7/1971 | U.S.S.R. . |
| 388738 | 9/1971 | U.S.S.R. . |
| 891076 | 12/1981 | U.S.S.R. . |
| 1822750 A1 | 7/1982 | U.S.S.R. . |
| 1600708 | 12/1995 | U.S.S.R. . |
| WO 95/08364 | 3/1995 | WIPO . |
| WO 95/10218 | 4/1995 | WIPO . |
| WO 95/15192 | 6/1995 | WIPO . |
| WO 95/16476 | 6/1995 | WIPO . |
| WO 96/10375 | 4/1996 | WIPO . |
| WO 96/17644 | 6/1996 | WIPO . |
| WO 96/25886 | 8/1996 | WIPO . |
| WO 96/30072 | 10/1996 | WIPO . |
| WO 96/30073 | 10/1996 | WIPO . |
| WO 96/32882 | 10/1996 | WIPO . |
| WO 97/12555 | 4/1997 | WIPO . |
| WO 97/13463 | 4/1997 | WIPO . |
| WO 97/13468 | 4/1997 | WIPO . |
| WO 97/13471 | 4/1997 | WIPO . |
| WO 97/26939 | 7/1997 | WIPO . |
| WO 97/37984 | 10/1997 | WIPO . |
| WO 97/40751 | 11/1997 | WIPO . |
| WO 98/06356 | 2/1998 | WIPO . |
| WO 98/07399 | 2/1998 | WIPO . |
| WO 98/10714 | 3/1998 | WIPO . |
| WO 98/15237 | 4/1998 | WIPO . |

(List continued on next page.)

OTHER PUBLICATIONS

"The Possibility Of Myocardial Revascularization By Creation Of A Left Ventriculocoronary Artery Fistula", by Ian Munro and Peter Allen, Canada, pp. 25–32, *Journal of Thoracic and Cardiovascular Surgery*, vol. 58, No. 1, Jul. 1969.

"The Current Status of Lasers in the Treatment of Cardiovascular Disease" by Jeffrey M. Isner and Richard H. Clarke, *IEEE*, vol QE–20, No. 12, Dec. 1984, pp. 1406–1420.

"The Possibility of Myocardial Revascularization by Creation of a Left Ventriculocoronary Artery Fistula", by Ian Munro and Peter Allen, M.D., *Journal of Thoracic and Cardiovascular Surgery*, vol. 58, No. 1, Jul. 1969, pp. 25–32.

*Primary Examiner*—Mickey Yu
*Assistant Examiner*—Kelly O'Hara
*Attorney, Agent, or Firm*—Westman, Champlin & Kelly, P.A.

[57] ABSTRACT

In order to bypass a restriction in a parent vessel, a first site in a branch vessel branching from the aorta is accessed intraluminally. An occlusion is formed at the first site, and the aperture is formed in the branching vessel, intraluminally, proximal of the first site. An aperture is formed in the parent vessel distal of the restriction, and a lumen is formed which communicates between the branching vessel proximal of the occlusion, and the parent vessel distal of the restriction.

14 Claims, 15 Drawing Sheets

U.S. PATENT DOCUMENTS

| | | |
|---|---|---|
| 3,667,069 | 6/1972 | Blackshear et al. . |
| 4,016,884 | 4/1977 | Kwan-Gett . |
| 4,165,747 | 8/1979 | Bermant . |
| 4,173,981 | 11/1979 | Mortensen . |
| 4,190,909 | 3/1980 | Ablaza . |
| 4,230,096 | 10/1980 | Zeff et al. . |
| 4,546,499 | 10/1985 | Possis et al. . |
| 4,562,597 | 1/1986 | Possis et al. . |
| 4,566,453 | 1/1986 | Kumano et al. . |
| 4,601,718 | 7/1986 | Possis et al. . |
| 4,610,661 | 9/1986 | Possis et al. . |
| 4,667,673 | 5/1987 | Li . |
| 4,690,684 | 9/1987 | McGreevy et al. . |
| 4,710,192 | 12/1987 | Liotta et al. . |
| 4,721,109 | 1/1988 | Healey . |
| 4,790,819 | 12/1988 | Li et al. . |
| 4,803,984 | 2/1989 | Narayanan et al. . |
| 4,808,163 | 2/1989 | Laub . |
| 4,819,640 | 4/1989 | Narayanan et al. . |
| 4,827,931 | 5/1989 | Longmore . |
| 4,907,591 | 3/1990 | Vasconcellos et al. . |
| 4,911,164 | 3/1990 | Roth . |
| 4,995,857 | 2/1991 | Arnold . |
| 5,011,469 | 4/1991 | Buckberg et al. . |
| 5,037,428 | 8/1991 | Picha et al. . |
| 5,047,039 | 9/1991 | Avant et al. . |
| 5,053,041 | 10/1991 | Ansari et al. . |
| 5,053,043 | 10/1991 | Gottesman et al. . |
| 5,061,245 | 10/1991 | Waldvogel . |
| 5,067,958 | 11/1991 | Sandhaus . |
| 5,080,663 | 1/1992 | Mills et al. . |
| 5,080,664 | 1/1992 | Jain . |
| 5,104,402 | 4/1992 | Melbin . |
| 5,122,154 | 6/1992 | Rhodes .................................. 623/12 X |
| 5,144,961 | 9/1992 | Chen et al. . |
| 5,222,962 | 6/1993 | Burkhart . |
| 5,222,963 | 6/1993 | Brinkerhoff et al. . |
| 5,222,971 | 6/1993 | Willard et al. . |
| 5,234,445 | 8/1993 | Walker et al. . |
| 5,254,113 | 10/1993 | Wilk . |
| 5,281,236 | 1/1994 | Bagnato et al. . |
| 5,282,810 | 2/1994 | Allen et al. . |
| 5,287,861 | 2/1994 | Wilk . |
| 5,308,320 | 5/1994 | Safar et al. . |
| 5,314,436 | 5/1994 | Wilk . |
| 5,314,472 | 5/1994 | Fontaine . |
| 5,323,789 | 6/1994 | Berggren et al. . |
| 5,330,486 | 7/1994 | Wilk . |
| 5,370,683 | 12/1994 | Fontaine . |
| 5,382,257 | 1/1995 | Lewis et al. . |
| 5,383,854 | 1/1995 | Safar et al. . |
| 5,383,928 | 1/1995 | Scott et al. . |
| 5,397,345 | 3/1995 | Lazarus . |
| 5,403,333 | 4/1995 | Kaster et al. . |
| 5,409,019 | 4/1995 | Wilk . |
| 5,425,705 | 6/1995 | Evard et al. . |
| 5,425,739 | 6/1995 | Jessen . |
| 5,425,765 | 6/1995 | Tiefenbrun et al. ...................... 623/12 |
| 5,429,144 | 7/1995 | Wilk . |
| 5,433,700 | 7/1995 | Peters . |
| 5,437,684 | 8/1995 | Calabrese et al. . |
| 5,441,507 | 8/1995 | Wilk . |
| 5,443,497 | 8/1995 | Venbrux . |
| 5,447,512 | 9/1995 | Wilson et al. . |
| 5,449,372 | 9/1995 | Schmaltz et al. . |
| 5,452,733 | 9/1995 | Sterman et al. . |
| 5,456,714 | 10/1995 | Owen . |
| 5,472,404 | 12/1995 | Volgushev . |
| 5,501,698 | 3/1996 | Roth et al. . |
| 5,522,884 | 6/1996 | Wright . |
| 5,527,319 | 6/1996 | Green et al. . |
| 5,527,324 | 6/1996 | Krantz et al. . |
| 5,536,251 | 7/1996 | Evard et al. . |
| 5,540,677 | 7/1996 | Sinofsky . |
| 5,540,701 | 7/1996 | Sharkey et al. . |
| 5,545,171 | 8/1996 | Sharkey et al. . |
| 5,554,162 | 9/1996 | DeLange . |
| 5,556,414 | 9/1996 | Turi . |
| 5,556,428 | 9/1996 | Shah . |
| 5,562,728 | 10/1996 | Lazarus et al. . |
| 5,569,272 | 10/1996 | Reed et al. . |
| 5,569,274 | 10/1996 | Rapacki et al. . |
| 5,571,090 | 11/1996 | Sherts . |
| 5,571,215 | 11/1996 | Sterman et al. . |
| 5,584,803 | 12/1996 | Stevens et al. . |
| 5,588,949 | 12/1996 | Taylor et al. . |
| 5,591,179 | 1/1997 | Edelstein . |
| 5,591,212 | 1/1997 | Keimel . |
| 5,593,424 | 1/1997 | Northrup, III . |
| 5,601,576 | 2/1997 | Garrison . |
| 5,601,581 | 2/1997 | Fogarty et al. . |
| 5,609,598 | 3/1997 | Laufer et al. . |
| 5,613,937 | 3/1997 | Garrison et al. . |
| 5,618,270 | 4/1997 | Orejola . |
| 5,643,292 | 7/1997 | Hart . |
| 5,653,744 | 8/1997 | Khouri . |
| 5,655,548 | 8/1997 | Nelson et al. . |
| 5,662,124 | 9/1997 | Wilk . |
| 5,662,711 | 9/1997 | Douglas . |
| 5,676,670 | 10/1997 | Kim . |
| 5,682,906 | 11/1997 | Sterrman et al. . |
| 5,685,857 | 11/1997 | Negus et al. . |
| 5,693,083 | 12/1997 | Baker et al. . |
| 5,702,368 | 12/1997 | Stevens et al. . |
| 5,702,412 | 12/1997 | Popov et al. ............................. 606/159 |
| 5,715,832 | 2/1998 | Koblish et al. . |
| 5,716,367 | 2/1998 | Koike et al. . |
| 5,718,725 | 2/1998 | Sterman et al. . |
| 5,722,426 | 3/1998 | Kolff . |
| 5,725,537 | 3/1998 | Green et al. . |
| 5,727,569 | 3/1998 | Benetti et al. . |
| 5,728,151 | 3/1998 | Garrison et al. . |
| 5,735,290 | 4/1998 | Sterman et al. . |
| 5,738,649 | 4/1998 | Macoviak . |
| 5,738,652 | 4/1998 | Boyd et al. . |
| 5,749,892 | 5/1998 | Vierra et al. . |
| 5,752,526 | 5/1998 | Cosgrove . |
| 5,755,682 | 5/1998 | Knudson et al. ........................... 604/8 |
| 5,755,687 | 5/1998 | Donlon . |
| 5,755,778 | 5/1998 | Kleshinski . |
| 5,758,663 | 6/1998 | Wilk et al. . |
| 5,766,151 | 6/1998 | Valley et al. . |
| 5,769,812 | 6/1998 | Stevens et al. . |
| 5,792,094 | 8/1998 | Stevens et al. . |
| 5,795,325 | 8/1998 | Valley et al. . |
| 5,797,920 | 8/1998 | Kim . |
| 5,797,933 | 8/1998 | Snow et al. . |
| 5,799,661 | 9/1998 | Boyd et al. . |
| 5,800,450 | 9/1998 | Lary et al. . |
| 5,800,522 | 9/1998 | Campbell et al. . |
| 5,849,036 | 12/1998 | Zarate ........................................ 623/1 |
| 5,868,770 | 2/1999 | Rugaard ................................. 606/167 |
| 5,893,369 | 4/1999 | LeMole .................................. 606/184 |
| 5,895,404 | 4/1999 | Ruiz ....................................... 606/185 |
| 5,904,147 | 5/1999 | Conlan et al. .......................... 128/899 |
| 5,904,690 | 5/1999 | Middleman et al. ................... 606/113 |

FOREIGN PATENT DOCUMENTS

| | | |
|---|---|---|
| WO 98/16161 | 4/1998 | WIPO . |
| WO 98/16174 | 4/1998 | WIPO . |
| WO 98/17182 | 4/1998 | WIPO . |
| WO 98/17187 | 4/1998 | WIPO . |

| | | | | | | |
|---|---|---|---|---|---|---|
| WO 98/19607 | 5/1998 | WIPO . | | WO 98/37814 | 9/1998 | WIPO . |
| WO 98/19634 | 5/1998 | WIPO . | | WO 98/52474 | 11/1998 | WIPO . |
| WO 98/19636 | 5/1998 | WIPO . | | WO 98/57591 | 12/1998 | WIPO . |
| WO 98/31302 | 7/1998 | WIPO . | | WO 98/57592 | 12/1998 | WIPO . |
| WO 98/32380 | 7/1998 | WIPO . | | WO 99/17683 | 4/1999 | WIPO . |
| WO 98/35626 | 8/1998 | WIPO . | | WO 99/18887 | 4/1999 | WIPO . |

PERCUTANEOUS BYPASS WITH BRANCHING VESSEL

INCORPORATION BY REFERENCE

The following U.S. patent applications are hereby fully incorporated:

U.S. patent application Ser. No. 08/813,038, entitled SYSTEM AND METHOD FOR PERCUTANEOUS CORONARY ARTERY BYPASS, filed on even date herewith and assigned to the same assignee as the present application pending; and U.S. patent application Ser. No. 08/812,879 and pending, entitled PERCUTANEOUS BYPASS BY TUNNELING THROUGH VESSEL WALL, filed on even date herewith and assigned to the same assignee as the present application.

BACKGROUND OF THE INVENTION

The present invention generally deals with vascular bypass methods. More specifically, the present invention deals with systems for performing percutaneous coronary artery bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are to diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs under visual observation. Such a technique is often referred to as minimally invasive direct coronary artery bypass (MIDCAB) (where the heart is not stopped) or heart port (where the heart is stopped), or if performed below the diaphragm, simply as laproscopic surgery. Such a system which is used to perform a bypass is disclosed in the Sterman et al. U.S. Pat. No. 5,452,733.

SUMMARY OF THE INVENTION

In order to bypass a restriction in a parent vessel, a first site in a branch vessel branching from the aorta is accessed intraluminally. An occlusion which may be permanent or temporary is optionally formed at the first site, and an aperture is formed in the branching vessel, intraluminally, proximal of the first site. An aperture is formed in the parent vessel distal of the restriction, and a conduit is provided to form a lumen which communicates between the branching vessel proximal of the occlusion, and the parent vessel distal of the restriction.

In one preferred embodiment, the lumen communicating between the branching vessel and the parent vessel comprises a graft introduced intraluminally into the branching vessel and connected between the branching vessel and the parent vessel. In another preferred embodiment, the branching vessel is severed proximal of the first site and the severed end of the branching vessel is attached to the parent vessel such that the branching vessel, itself, forms the conduit between a proximal portion of the branching vessel and the parent vessel distal of the restriction.

DETAILED DESCRIPTION OF THE PREFERRED EMBODIMENTS

Figure 1A:
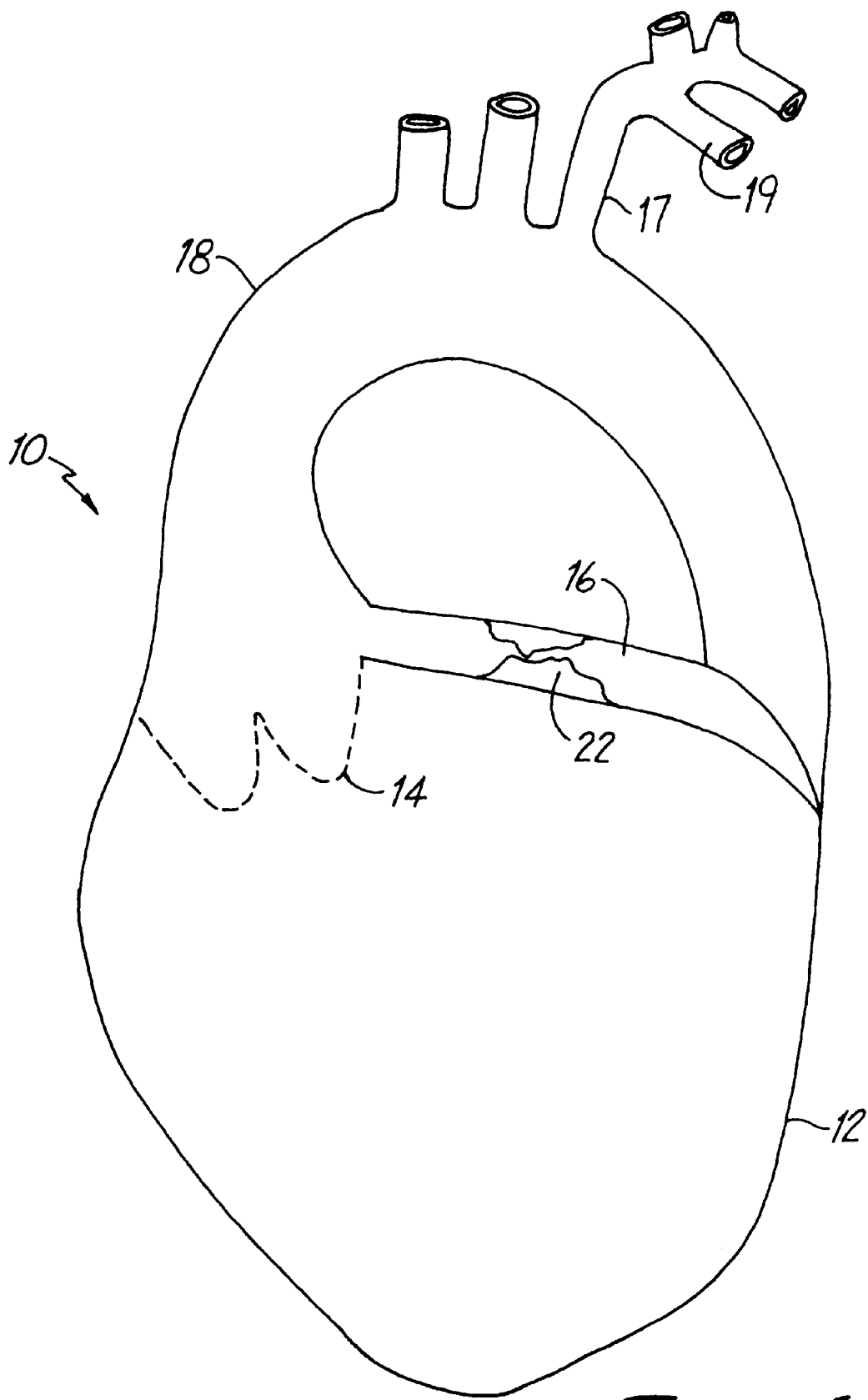
FIGS. 1A and 1B illustrates a portion of a vascular system with a parent vessel having a restriction.

FIG. 1A illustrates a portion of a vascular system 10. System 10 includes heart 12, heart valve 14, coronary artery 16, aorta 18 and a plurality of branching vessels, branching from aorta 18. Two of the branching vessels illustrated in FIG. 1A include subclavian artery 17, and internal mammary artery (IMA) 19.

Coronary artery 16 includes restriction 22. While restriction 22 is shown in FIG. 1A as being a total occlusion, restriction 22 can be any disease including complete occlusion, or simply a stenotic lesion. The present invention is utilized to bypass restriction 22 in artery (or parent vessel) 16 by using a branching vessel as a source for blood flow to parent vessel 16.

Figure 1B:
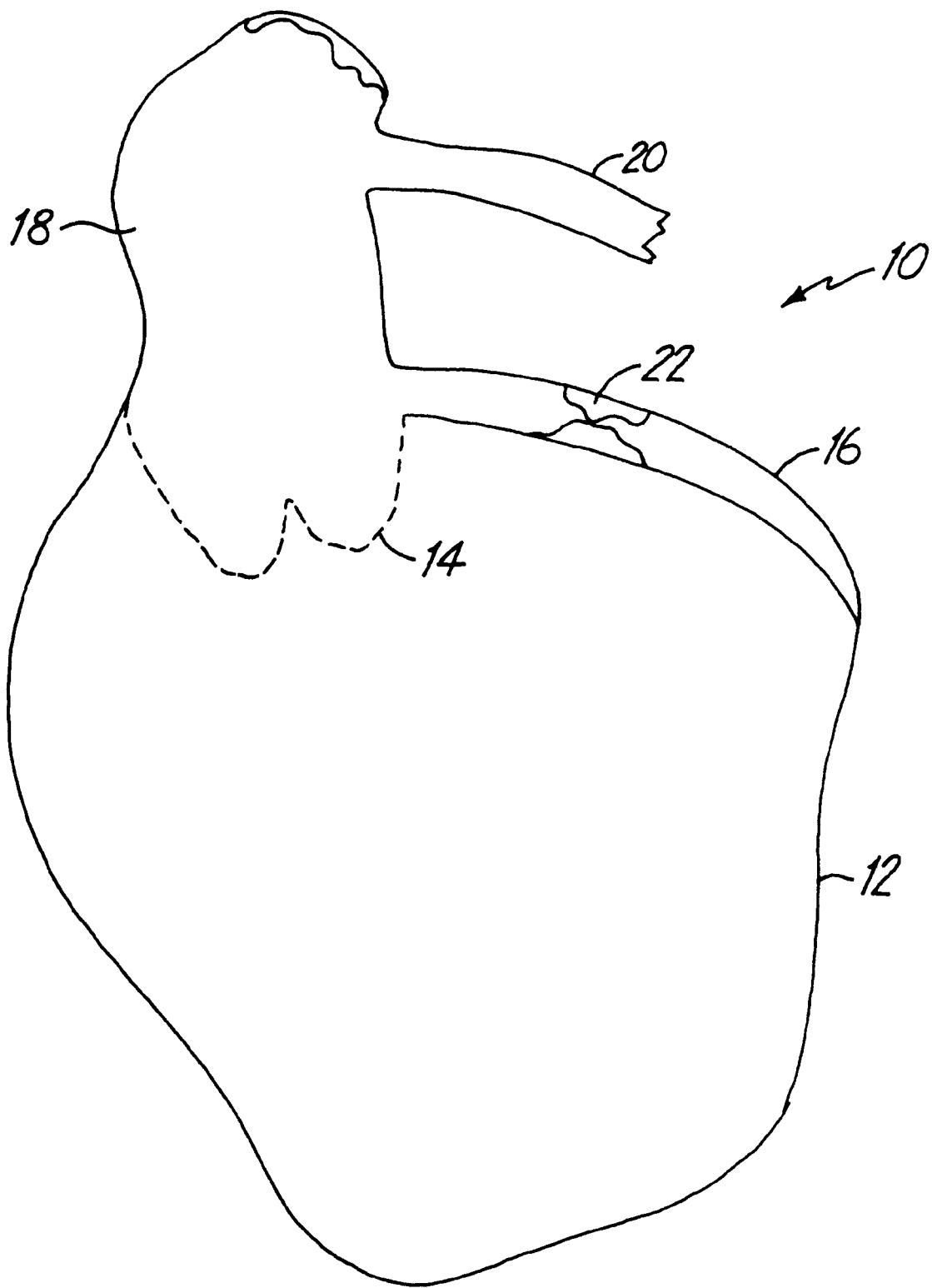

FIG. 1B illustrates a portion of vascular system 10. FIG. 1B illustrates a branching vessel 20. Although branching vessel 20 is shown coming from the ascending aorta, this is primarily for purposes of clarity. It will be understood that most branching vessels originate from the aortic arch, or the descending aorta, but the present description will proceed with respect to branching vessel 20, for the purposes of clarity only. It should be noted that, the term branching vessel as used in the present description contemplates any vessel which branches, directly or indirectly, from the aorta, and which can be used to supply blood flow as described herein, without detrimentally affecting another portion of the body. It will also be noted that the IMA 19 is a preferred branching vessel for use in accordance with the present invention because the blood flow through the IMA 19 is provided to a region of the body which also has collateral or backup flow. Therefore, if blood flow from the IMA 19 is removed, the region served by the IMA will obtain sufficient blood flow from other sources. However, the remainder of the present description will proceed with respect to branching vessel 20 which will be understood to be any suitable branching vessel in the vasculature.

Figure 2:
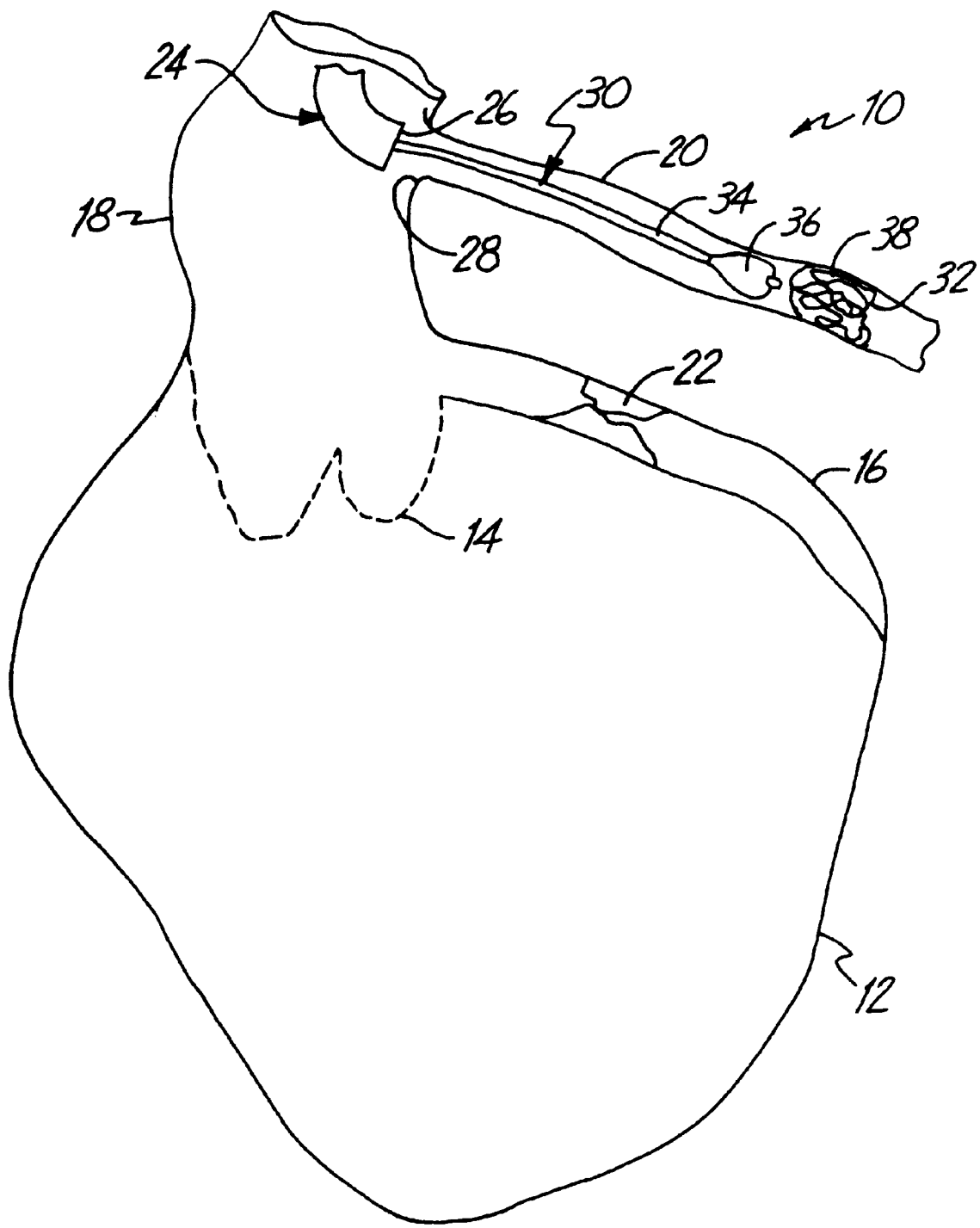
FIG. 2 illustrates the vascular system of FIG. 1B with an occlusion formed in a branching vessel, branching from the aorta.

FIG. 2 illustrates a first portion of a procedure used to bypass restriction 22 in accordance with one preferred embodiment of the present invention. FIG. 2 illustrates that a standard guide catheter 24 is first advanced through aorta 18 (preferably initially through a femoral artery and then through the systemic vasculature up to, and through, aorta 24). In a preferred embodiment, the distal end 26 of guide catheter 24 is positioned such that it is closely proximate an ostium 28 of branching vessel 20. Then, an occlusion forming device 30 is advanced through guide catheter 24. Occlusion forming device 30 is advanced out of the distal end 26 of guide catheter 24, through ostium 28 of vessel 20 and through vessel 20 to an occlusion site 32. Of course, in the embodiment in which branching vessel 20 comprises IMA 19, the guide catheter 24 and occlusion device 30 must be advanced through subclavian artery 17 in order to access IMA 19.

In one preferred embodiment, occlusion device 30 comprises an elongate portion 34 which supports a heated balloon 36. Heated balloon 36 is advanced to site 32 and is then activated so that it cauterizes vessel 20 at site 32, thereby creating a total occlusion 38 at site 32.

In another preferred embodiment, occlusion device 30 is simply a delivery catheter which is used to deliver coils, collagen, or another suitable material to site 32 in vessel 20 to create occlusion 38.

Figure 3:
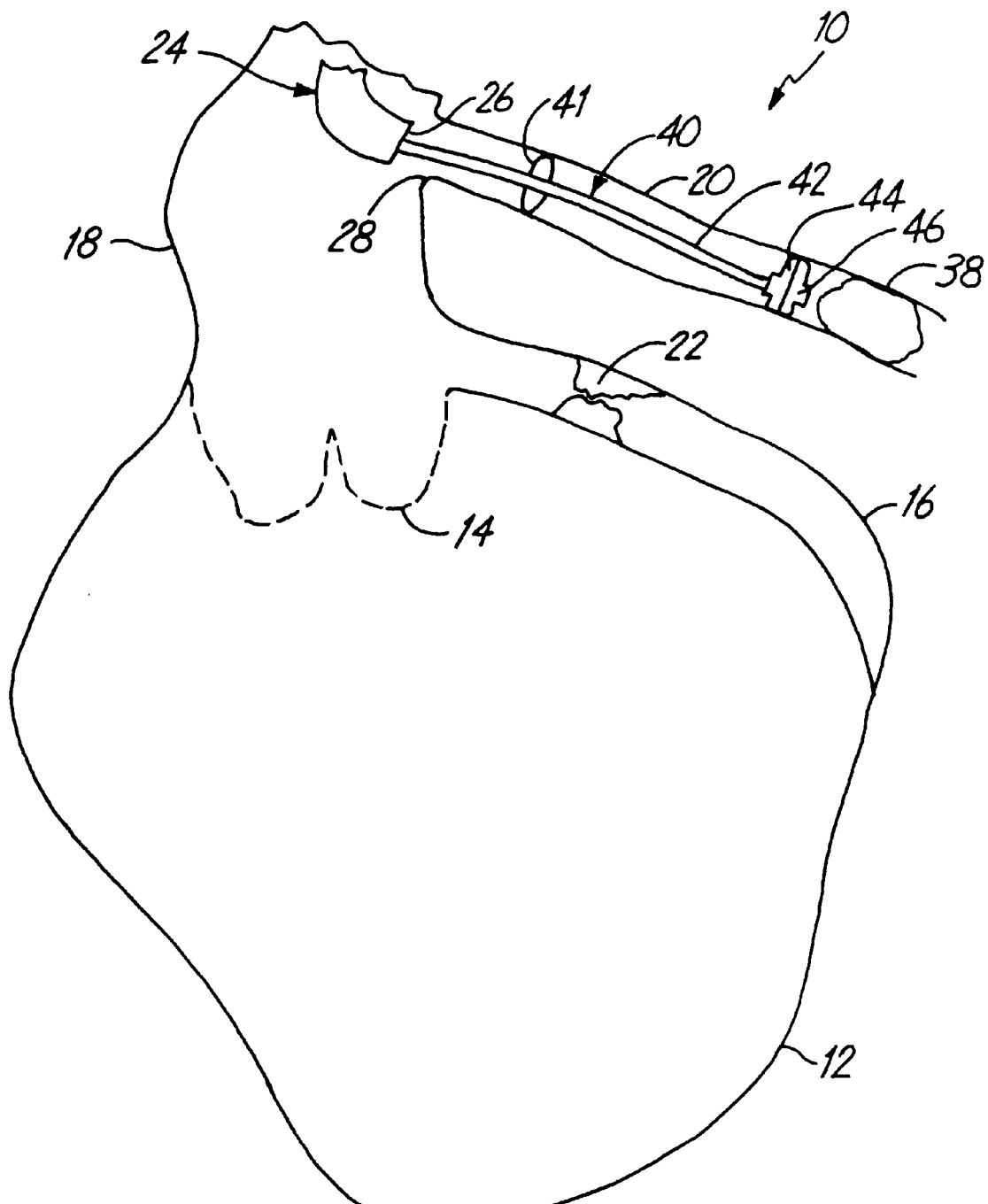
FIG. 3 illustrates severing the branching vessel in accordance with one aspect of the present invention.

It should be noted that occlusion 38 at site 32 is not required and, if utilized, may be either a permanent or temporary occlusion. In any case, after occlusion 38 has been formed, occlusion device 30 is withdrawn from system 10, through guide catheter 24. FIG. 3 illustrates a next step in bypassing restriction 22 in accordance with one aspect of the present invention. FIG. 3 illustrates that cutting device 40 is next placed in vessel 20, just proximal of occlusion 38. Cutting device 20 is used to occlude vessel 20 proximal of site 32 and to sever vessel 20. In the preferred embodiment, cutting device 40 preferably includes an elongate member 42 with a proximal occlusion balloon 41 and a distal balloon, or other expandable member 44. In addition to balloon 41, heart 12 can be stopped. Other occlusion devices can be placed in vessel 20 proximal of the site at which vessel 20 is severed. However, occluding balloons have a relatively low instance of emboli formation, and therefore have a lower instance of neurological problems which result from the formation of emboli. Any other suitable technique for preventing flow out of vessel 20 after it is severed can also be used.

The distal tip 46, or an outer periphery of expandable member 44, is preferably provided with a cutting edge, or cutting blade which can be rotated by manipulation of the physician, in order to cut through the walls of vessel 20. Expandable member 44 can preferably be retained in the expanded position during the cutting procedure. This serves to occlude vessel 20 after it has been severed.

In addition, it should be noted that cutting device 40 can be the same device as occlusion device 30. In that case, inflatable member 44 is preferably a cauterizing balloon as described with respect to FIG. 2.

Figure 4:
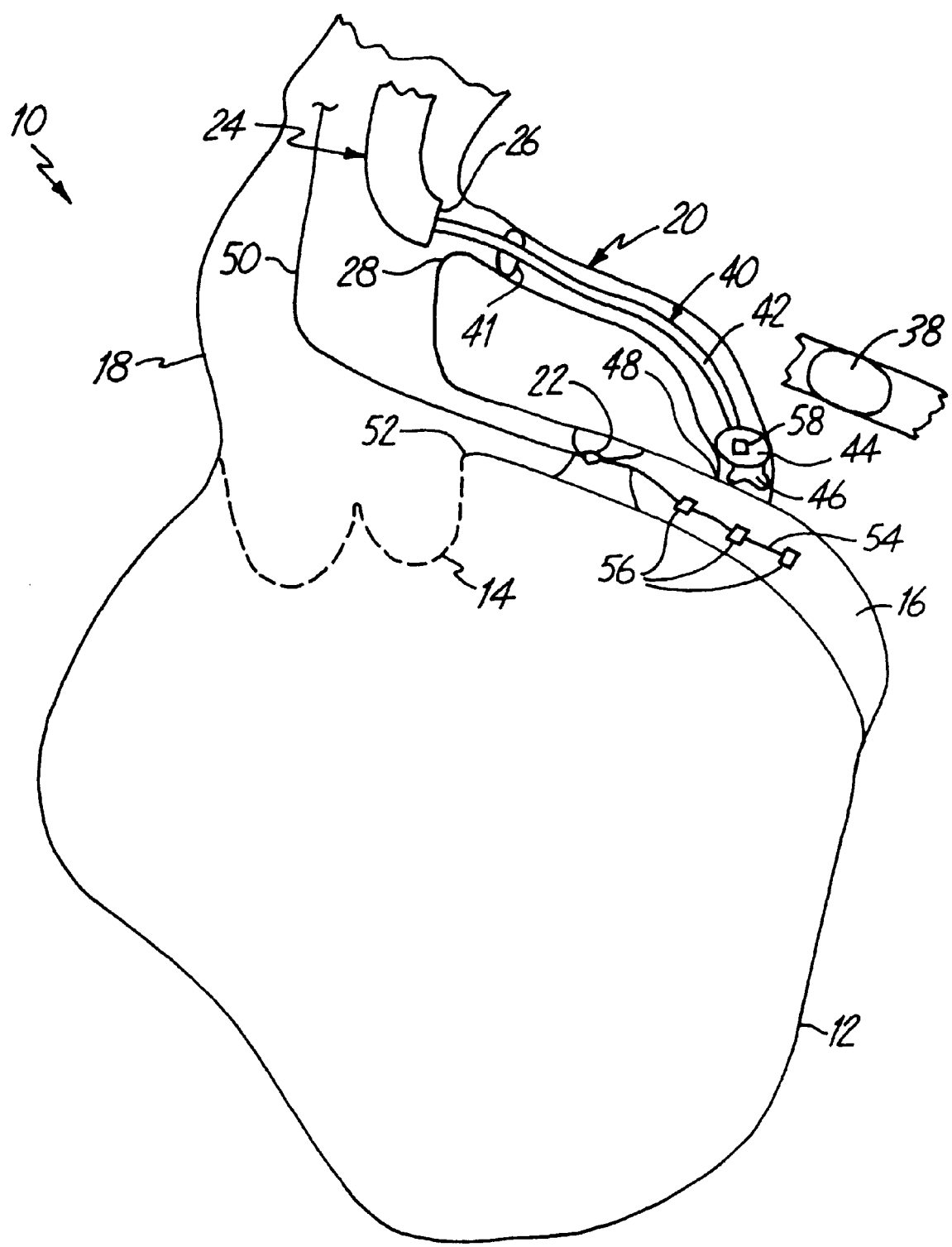
FIG. 4 illustrates positioning of the severed branching vessel shown in FIG. 3 proximate the restricted vessel, distal of the restriction.

FIG. 4 illustrates a next step in bypassing restriction 22 in accordance with one aspect of the present invention. FIG. 4 illustrates that, once vessel 20 has been severed proximal of occlusion 38, severed end 48 of vessel 20 is directed, or steered, toward a region in artery 16 distal of restriction 22. Where branching vessel 20 is one such as the IMA which is embedded in tissue, it must be separated from that tissue prior to being steered toward artery 16. This can be done using a suitable dissection system, such as using known devices to perform the dissection via a thoracic approach. Severed end 48 of vessel 20 can be steered in any number of suitable ways. For example, a steerable guidewire or steerable catheter can be used to steer severed end 48. In addition, cutting device 40 may preferably be a fully articulated catheter which can be steered and maneuvered in the interstitial spaces between vessel 20 and vessel 16.

Figure 4A:
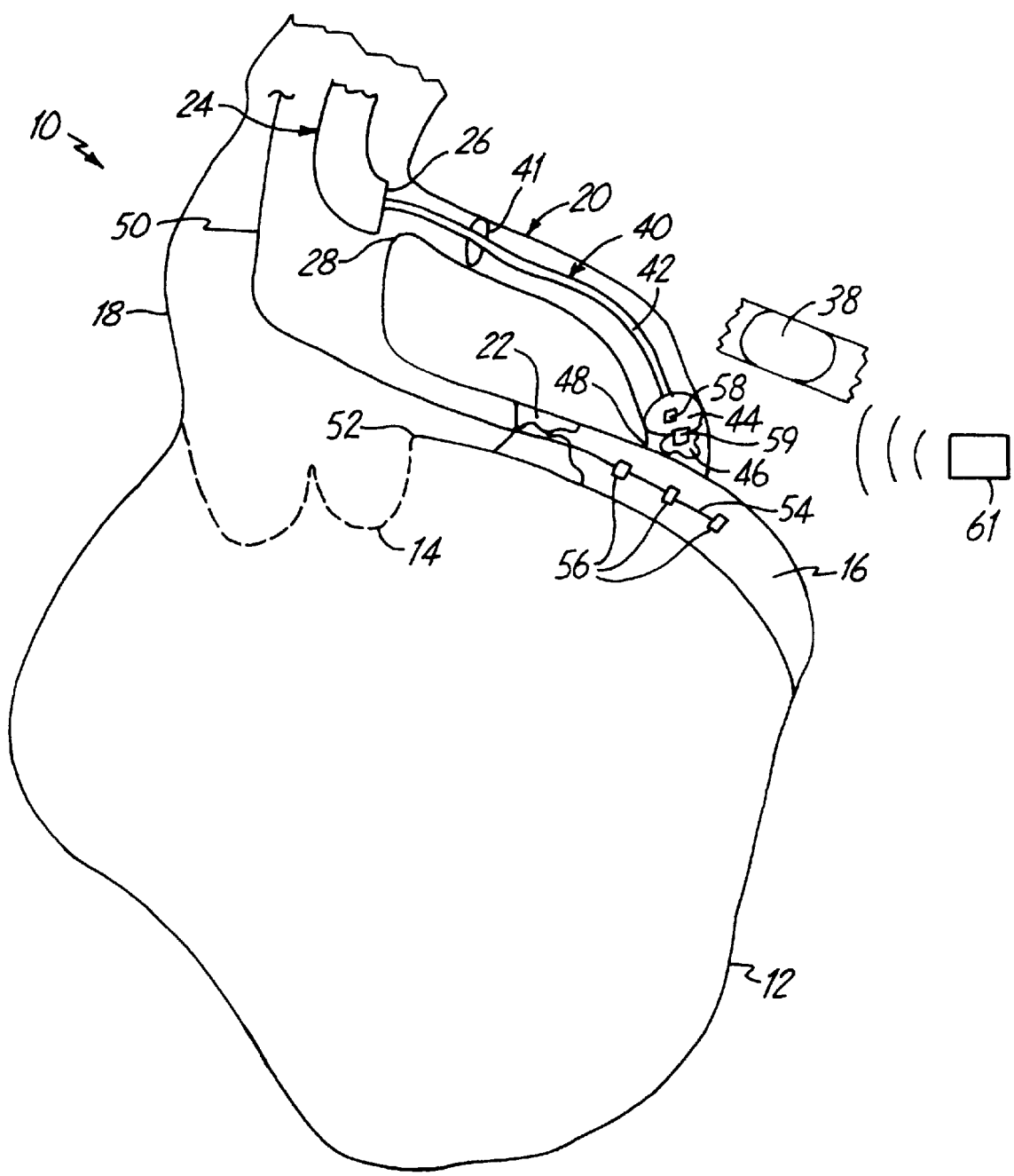
FIG. 4A illustrates manipulation of the branching vessel into the position shown in FIG. 4.

FIG. 4A illustrates another preferred embodiment, other than a fully articulated catheter, for manipulating severed end 48 to be adjacent the outer surface of vessel 16. In FIG. 4A, cutting device 40 is provided with a piece 59 of magnetic material which is securely attached thereto. A second magnetic piece 61 is manipulated by the physician such that manipulation of piece 61 causes corresponding movement of severed end 48 through the magnetic attraction between pieces 59 and 61. This manipulation is done under suitable observation as discussed in greater detail below until severed end 48 is located appropriately on the exterior of vessel 16 in a region distal of restriction 22.

In yet another preferred embodiment, severed end 48 is guided through a thoracoscope. The physician preferably inserts the thorascope into the chest cavity to assist in guiding severed end 48 to the appropriate location. However, any other suitable system for steering severed end 48 can be used.

In order to properly guide severed end 48 of vessel 20 to the region in vessel 16 distal of restriction 22, the physician must employ some means of observing the spatial relationship between severed end 48 and the region distal of restriction 22 in vessel 16. This can be accomplished in any number of suitable ways. For example, as shown in FIG. 4, cutting device 40 is preferably formed of radiopaque material, or at least has radiopaque markings near the distal end thereof. Therefore, when restriction 22 is not a total occlusion, contrast fluid is injected through vessel 16 to locate restriction 22. The position of restriction 22 relative to severed end 48 (and cutting device 40) is then observed. Alternatively, a wire or fiber 50 is advanced across restriction 22 and has radiopaque markings at its distal end. Cutting device 40 is moved toward the markings under fluoroscopic observation.

In another preferred embodiment, restriction 22 is crossed with a conductive wire or fiber 50 which is intraluminally advanced through aorta 18, through an ostium 52 of vessel 16, and across restriction 22. Conductive wire or fiber 50 preferably includes, at its distal end 54, a plurality of sensors 56. In addition, the distal end of cutting device 40 is preferably provided with transmitter 58. In one preferred embodiment, transmitter 58 includes one of an ultrasound transmitter, radiofrequency transmitter, a plurality of point light sources, or a single intense point light source, or an electromagnetic transmitter (such as where current is actively applied to a coil to induce a magnetic field thereabout). Receivers (or sensors) 56 are suitable devices which are compatible with transmitter 58 so that receivers 56 receive or sense the signals provided by transmitter 58.

For instance, where transmitter 58 includes an inductive magnetic coil, receivers 56 form a magnetic sensor array to receive the signals induced in the coil. When transmitter 58 includes an ultrasound transmitter, receivers 56 form an ultrasound imager so that the relative positioning of receivers 56 and transmitter 58 can be determined by the physician. When transmitter 58 includes a single point light source, or an array of point light sources, receivers 56 are formed as an imaging fiber optic bundle which detect the light emitted by the light source or light sources forming transmitter 58. In addition, when transmitter 58 includes an RF transmitter, for example, receivers 56 are formed as a directional antenna. In any of the above cases, or similar cases, the relative position between transmitter 58 and receivers 56 can be determined so that the severed end 48 of vessel 20 can be properly located relative to vessel 16, such that severed end 48 can be positioned proximate a region of vessel 16 which is distal to restriction 22. It should also be noted that transmitter 58 can be placed in parent vessel 16 and receivers 56 can be placed at the severed end 48 of vessel 20.

In another preferred embodiment, location of various items within the vasculature is accomplished using a triangulation and coordinate mapping system. In that embodiment, a radio frequency (RF) emitter is placed in the heart, or in the vasculature near the heart. The RF emitter is preferably placed on a catheter or another device, the placement of which must be guided. A number of reference electrodes (or receivers) are placed on the outside of the body at various points on the chest and back. In the preferred embodiment, three reference receivers are placed on the exterior of the body, two on the chest on opposite sides of the heart and one on the back. The three receivers are used to triangulate on the RF transmitter located on the device within the vasculature. Three dimensional modeling can be used, along with known motion and analysis techniques to determine the placement and motion of the RF transmitter within the vasculature. Such a system can be used to obtain true position and the relative positions of different objects in the vasculature. Of course, a higher frequency signal could also be used, and a similar device could be used in which magnetic sensing devices are employed.

If occlusion 22 is not total, vessel 16 is totally occluded prior to entry into vessel 16 distal of occlusion 22. Such occlusion can be accomplished by any suitable means, such as balloon cauterization, delivery of collagen, coils, an occlusion balloon or other suitable occlusion techniques.

In any case, once the severed end 48 of vessel 20 is properly positioned, cutting device 40 is used to form an aperture in vessel 16 distal of restriction 22. Severed end 48 is then attached to vessel 16 in the region proximate the aperture therein so that the lumen of vessel 20 communicates with the lumen of vessel 16 distal of restriction 22. In one preferred embodiment, severed end 48 is attached about the aperture formed in vessel 16 using in intraluminal suturing catheter. Intraluminal suturing devices are described in greater detail in the following U.S. Pat. No. 5,080,663 entitled SEWING DEVICE; U.S. Pat. No. 5,364,389 entitled METHOD AND APPARATUS FOR SEALING AND/OR GRASPING LUMINAL TISSUE; U.S. Pat. No. 5,545,171 entitled ANASTOMOSIS CATHETER; and U.S. Pat. No. 5,591,179 entitled ANASTOMOSIS SUTURING DEVICE AND METHOD and, which are hereby incorporated by reference.

Figure 5:
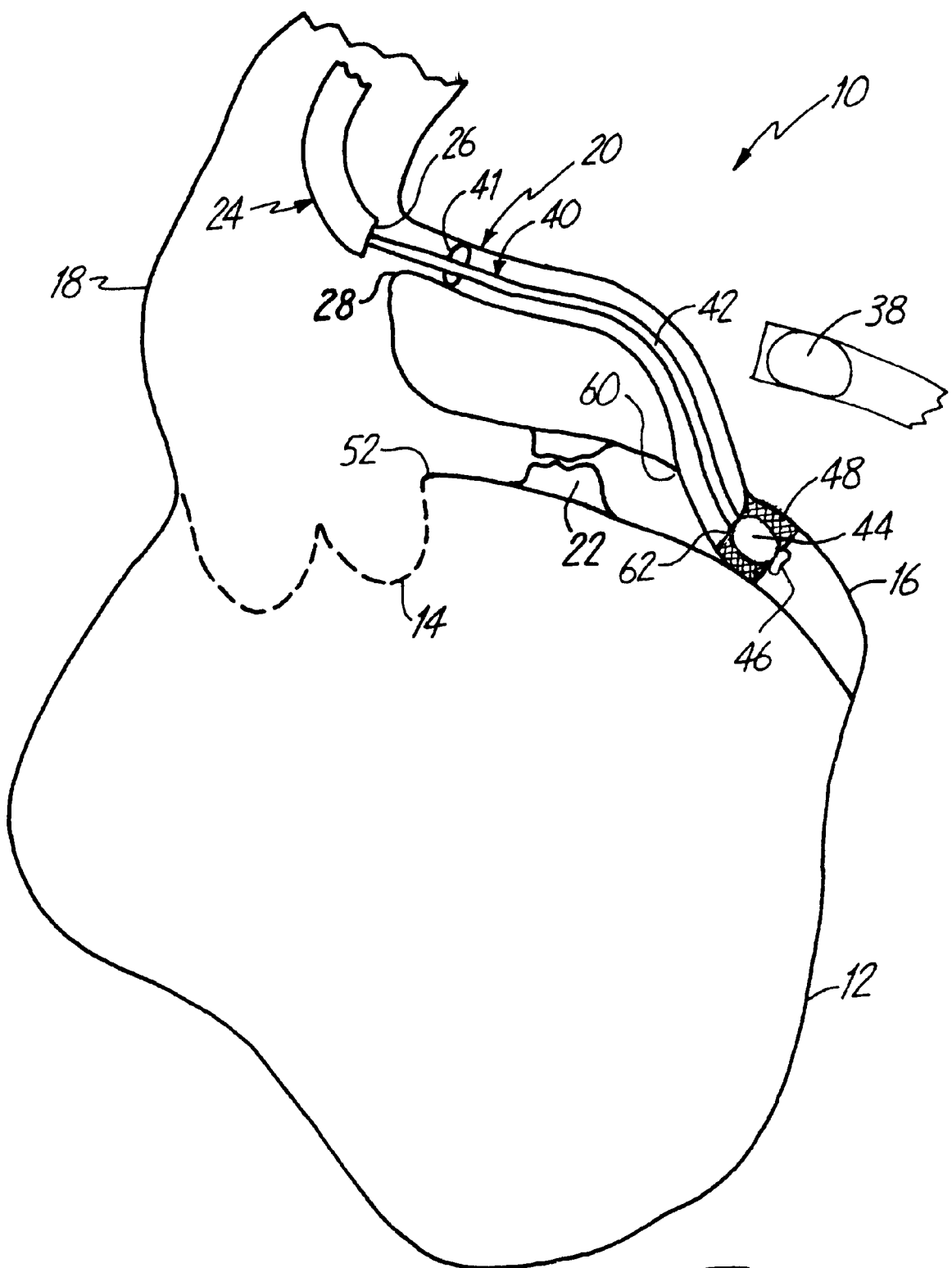
FIG. 5 illustrates insertion of a severed end of the branching vessel shown in FIG. 3 into the restricted vessel, distal of the restriction.

In another preferred embodiment, severed end 48 is inserted through the aperture 60 formed in vessel 16, and into the lumen of vessel 16. This is illustrated in FIG. 5. Severed end 48 of vessel 20 is then attached within vessel 16 such that the lumen of vessel 20 communicates with the lumen of vessel 16 distal of restriction 22. In one preferred embodiment, a stent 62 is inserted in the severed end 48 of vessel 20 and expanded to form an anastomosis in vessel 16. Expandable member 44 is used to expand or deploy stent 62 such that the outer diameter of severed end 48 closely approximates, and frictionally fits within, the inner diameter of lumen 16. In another embodiment, stent 62 is loaded with a glue or other suitable adhesive material which is used to hold severed end 48 within vessel 16. In yet another embodiment, mechanical hooks or metal clamps are used to secure the severed end 48 and/or stent 62 within vessel 16.

Figure 6:
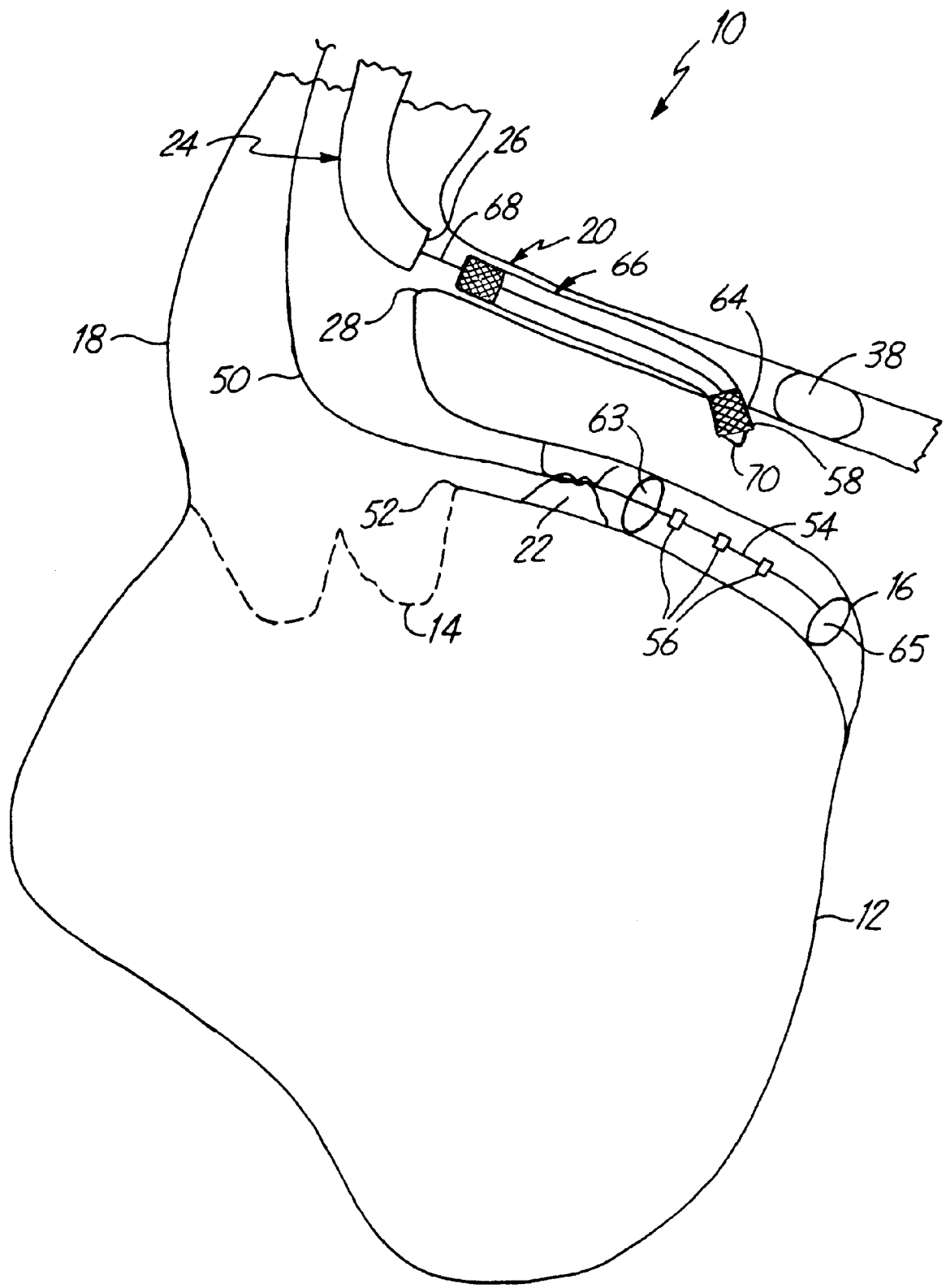
FIG. 6 illustrates manipulation of a graft between the branching vessel and the restricted vessel.

FIG. 6 illustrates another aspect of the present invention. In FIG. 6, rather than severing vessel 20 and inserting the severed end of vessel 20 into vessel 16, an aperture 64 is simply formed in vessel 20. Then, a graft 66 is passed through guide catheter 24, over a wire 68, and through the aperture 64 in vessel 20. Wire 68 preferably has a cutting probe advanced thereover with cutting tip 70 (or an introducer tip) at its distal end which is used to form the aperture in vessel 20. The distal tip 70 of the cutting probe is then steered toward the appropriate exterior region of vessel 16 distal of restriction 22. Distal tip 70 is then used to form an aperture in vessel 16 for the insertion of the distal end of graft 66 therein to form an anastomosis in vessel 16. FIG. 6 also illustrates that wire 60 is optionally provided with a pair of occlusion balloons or other suitable devices 63 and 65 which are used to occlude flow in vessel 16 during deployment of graft 66.

Figure 7A:
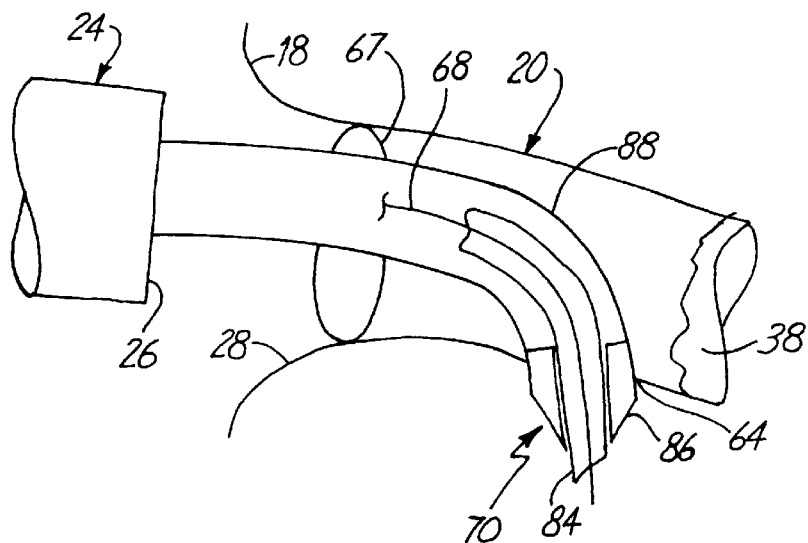
FIGS. 7A and 7B illustrate a system and method for deploying the graft shown in FIG. 7 between the branching vessel and the restricted vessel.
Figure 7B:
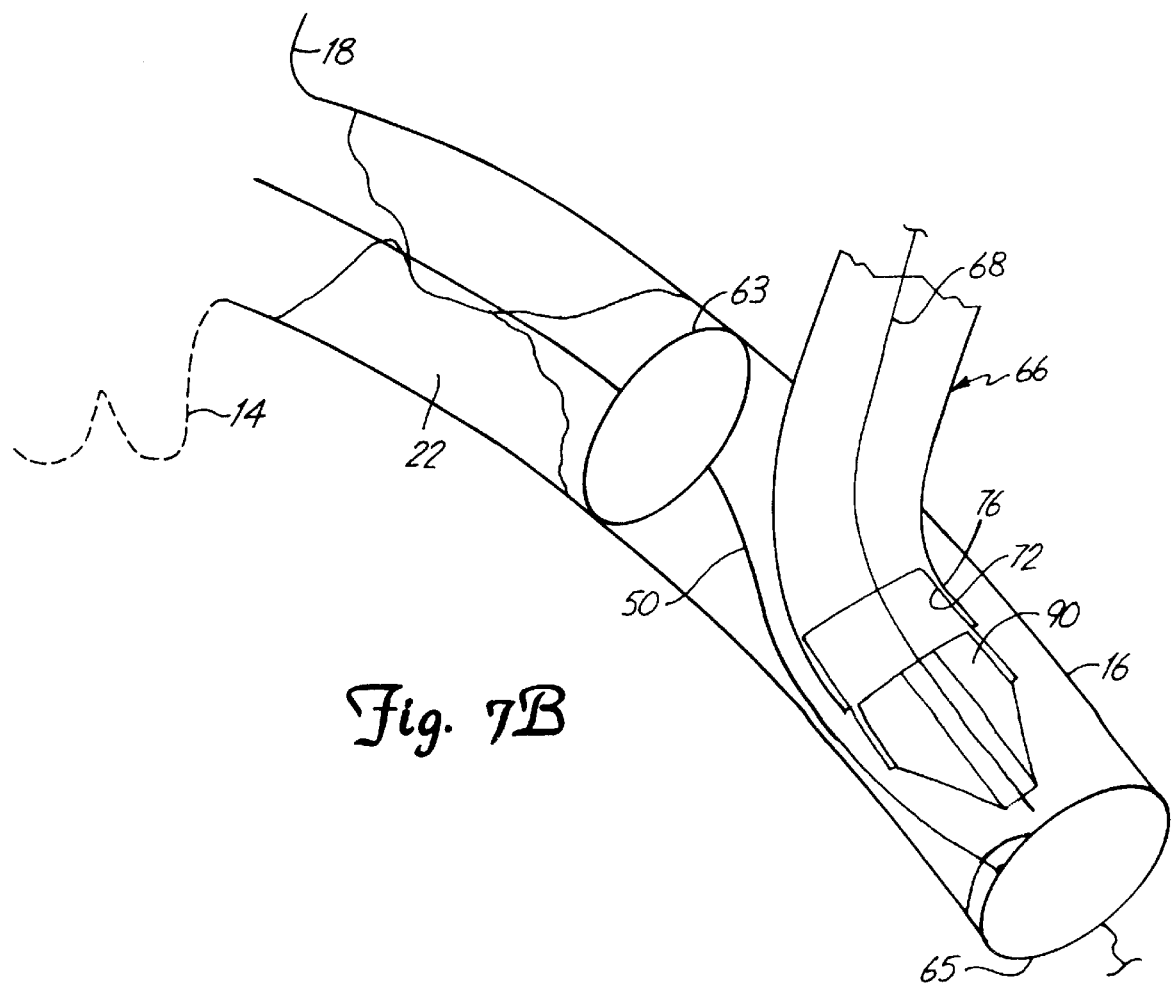
Figure 7:
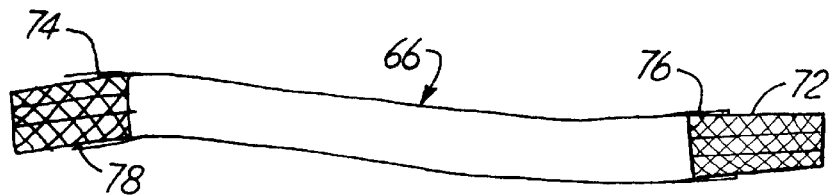
FIG. 7 is an enlarged view of one embodiment of a graft in accordance with the present invention.

FIG. 7 better illustrates graft 66. FIG. 7 shows that, in the preferred embodiment, a pair of stents 72 and 74 are provided at the ends of graft 66. Stents 72 and 74 are preferably formed of an expandable, woven, braided, or mesh material which can be selectively expanded to have a preselected or variable outer diameter which approximates the inner diameter of the vessel or aperture within which it is deployed. End 76 of graft 66 is preferably attached to either the inner or outer surface of stent 72, and end 78 of graft 66 is preferably attached to either the inner or outer surface of stent 74. The connections between the stents and the graft 66 can be accomplished in any number of suitable ways, such as through the use of an appropriate adhesive, such as weaving the stent directly into the graft material, such as by forming a frictional fit therebetween, or by utilizing another suitable connection mechanism.

In the preferred embodiment, the body of graft 66 is preferably either a biologically compatible, artificial graft (such as PTFE material), or a section of a human vein, such as a saphenous vein graft.

FIGS. 7A and 7B illustrate in greater detail the manner in which graft 66 is deployed within vessel 20 and native vessel 16. Prior to performing the method illustrated herein the patient may be placed on full cardiopulmonary bypass and heart 12 is stopped. Alternatively, the heart need not be stopped and occlusion balloons 63 and 65 (shown in FIG. 6) and proximal occlusion balloon 67 are deployed to stop blood flow in the relevant vasculature. Another occlusion balloon such as 65 (shown in FIG. 6) may optionally be provided on the distal region of a guidewire 68 which is advanced through graft 66. Other systems and methods to halt blood flow can also be used. Guide catheter 24 is then inserted into aorta 14 and guidewire 68 is advanced through guide catheter 24. The cutting probe having tip 70 is advanced over guidewire 68. Tip 70 includes a cutting needle 84 and a dilator sheath 86. A catheter 88 is used to advance tip 70 over wire 68. In the preferred embodiment, needle 84 is used to make an incision, or aperture 64 in the wall of vessel 20. Dilator sheath 86 is then advanced through the incision 64. Catheter 88 is preferably a fully articulated catheter with an ultrasonic tip, or with a fiberoptic tip, or with other suitable system for observing tip 70 during movement.

In any case, tip 70 is moved adjacent native vessel 16. Needle 84 is then again advanced over wire 68 and native vessel 16 is pierced. Wire 68 is advanced into native vessel 16 and contrast fluid is preferably injected. Tip 70 is then advanced over wire 68 to the region in vessel 16 distal of occlusion 22. This is shown in FIG. 7B.

Contrast fluid is preferably injected to verify the position of tip 70 distal of occlusion 22 in native vessel 16. Wire 68 is held in place in native vessel 16, as shown in FIG. 7B, and the remainder of tip 70 is removed. Another introducer tip 90, along with graft 66, is then advanced over wire 68. Introducer tip 90 is advanced through aperture 64 and vessel 20 and through the aperture in vessel 16, and carries with it graft 66 to the position shown in FIG. 7B. Proper placement of stent 72 within vessel 16 is verified through the injection of contrast medium.

Figure 8:
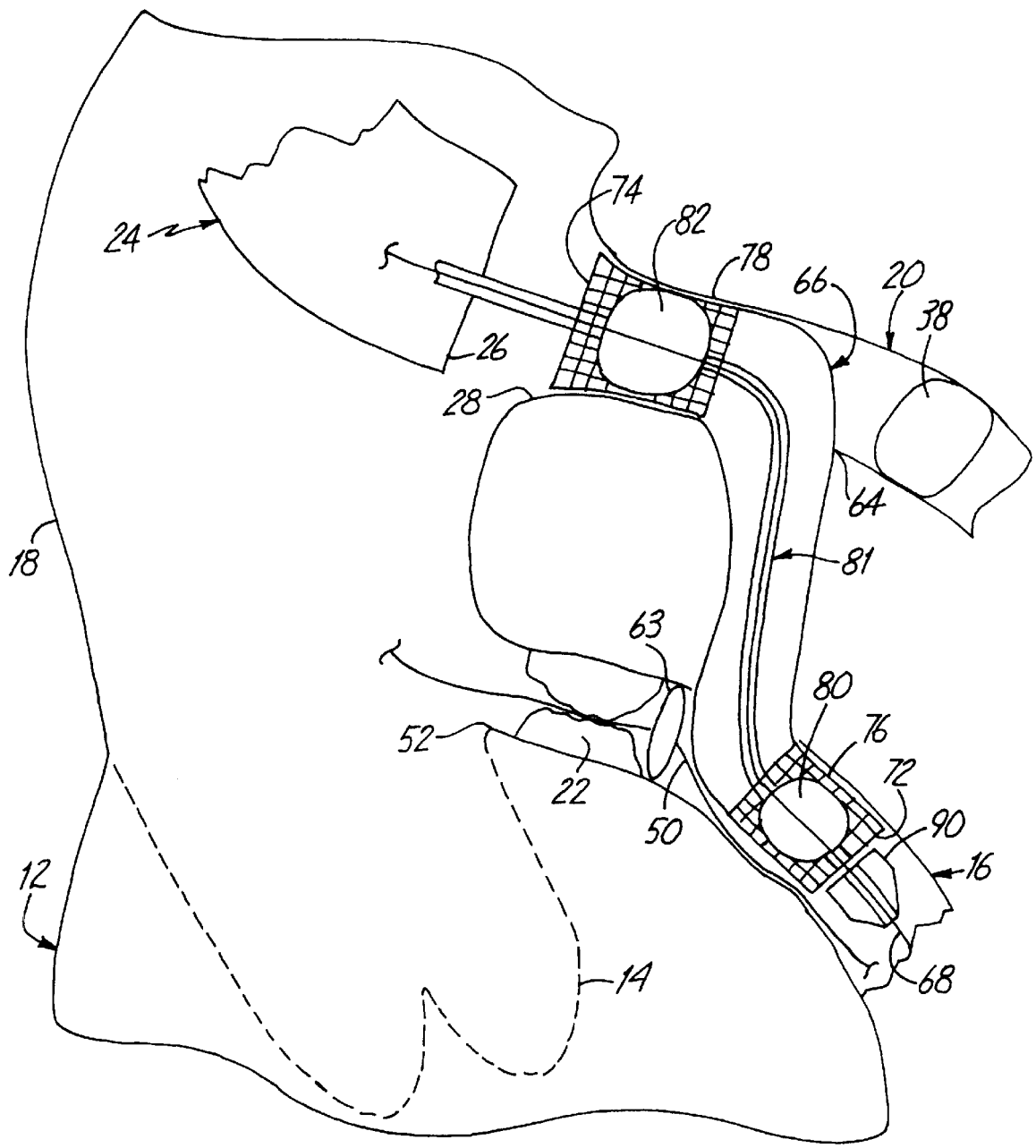
FIG. 8 illustrates deployment of the graft shown in FIG. 7 in accordance with one aspect of the present invention.

A balloon catheter system, either inserted along with graft 66, or after graft 66 is located in the position shown in FIG. 7B, is then deployed. Such balloon catheter system is shown in greater detail in FIG. 8. The balloon catheter system 81 includes distal balloon 80 and proximal balloon 82. The balloons are placed such that, when properly deployed, distal balloon 80 lies within the interior of stent 72 and proximal balloon 82 lies within the interior of stent 74. Alternatively, the different balloons can be independently movable and positioned relative to one another.

Once in place, balloons 80 and 82 are expanded. Balloon 80 is first inflated to expand stent 72 to low pressure, and distal occlusion balloon 65, which is attached to wire 50, is deflated and removed. Balloons 80 and 82 are then expanded to such a degree that stents 72 and 74 expand radially outwardly so that the exterior of the stents achieves an outer diameter which closely approximates the inner diameter of the vessel within which it is deployed. This causes a frictional fit between the outer surface of the stents 72 and 74 (or the ends of graft 66) and the inner surface of the lumens within which they are deployed. In addition, a suitable adhesive or glue can be applied to the stents 72 and 74 to further facilitate anastomosis in the vessels in which they are deployed.

It should, however, be noted that deployment of stent 66 can be performed in other manners. For example, balloons 80 and 82 can be placed within the interiors of stents 72 and 74, respectively, prior to insertion of graft 66 into the vascular system 10. In that case, balloons 80 and 82 would preferably form an assembly insertable with wire 68 during the procedure. Alternatively, stent 66 can be deployed using only a single inflatable member. In that case, the single inflatable member would first be placed within the interior of one of stents 72 and 74 in the deflated position and then inflated to secure the respective stent in the appropriate vessel. The balloon is then moved to reside within the other stent 72 or 74 where it is inflated to deploy that stent in the appropriate vessel as well.

Figure 9A:
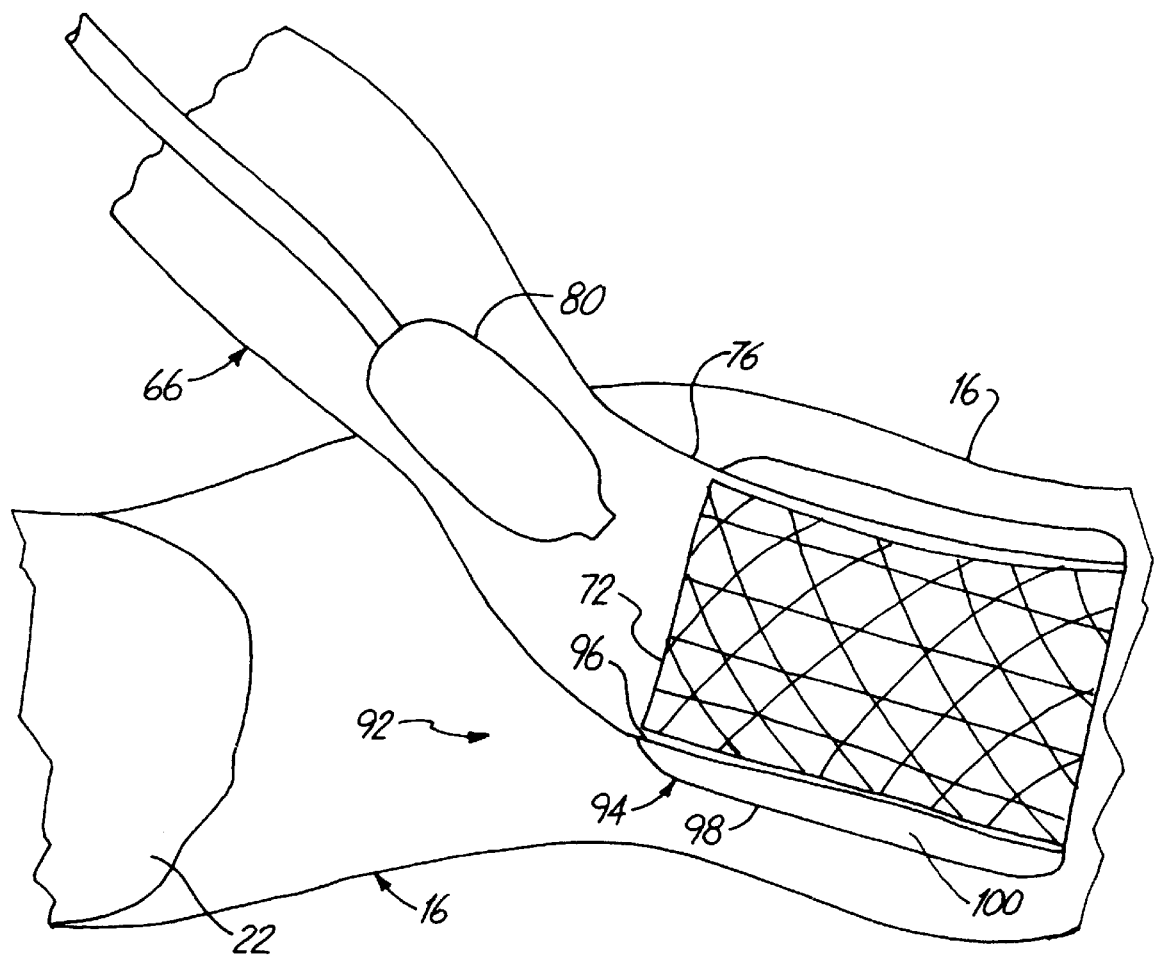
FIGS. 9A and 9B illustrate a system and method for forming an anastomosis in a bypass procedure in accordance with one aspect of the present invention.
Figure 9B:
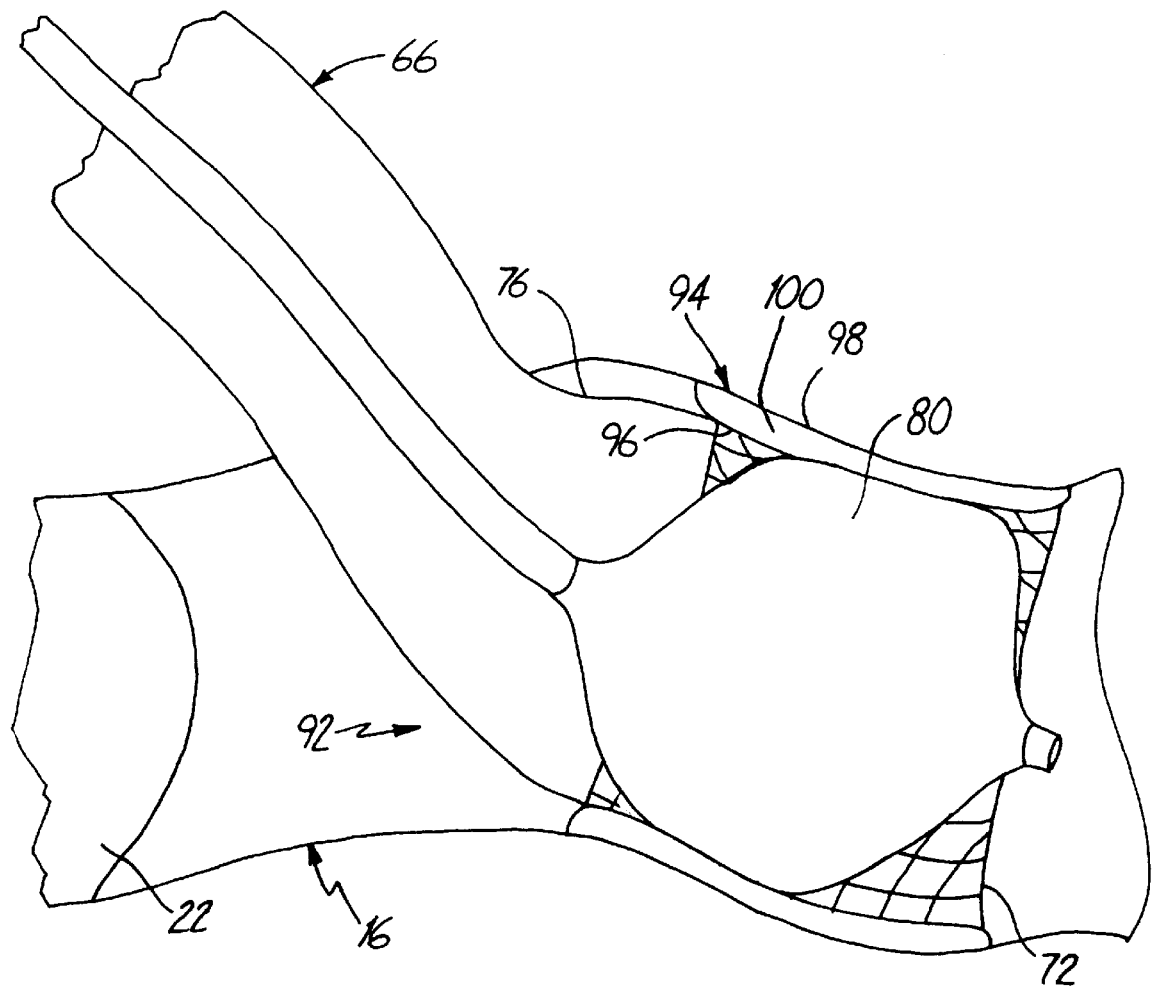

FIGS. 9A and 9B illustrate yet another aspect of the present invention. For the purposes of illustration of this aspect of the invention, a distal portion 92 of graft 66 is deployed within vessel 16, distal of occlusion 22. In the embodiment shown in FIGS. 9A and 9B, distal portion 92 of graft 66 includes end 76 of the graft 66, along with stent 72. The outer diameter of distal portion 92 of graft 66 preferably includes sheath 94. Sheath 94 preferably has an inner radial surface 96 which is impermeable to fluid flow, and an outer surface 98 which, when rendered discontinuous or broken, is permeable to fluid flow. Sheath 94 preferably includes a central portion 100, between inner surface 96 and outer surface 98, which contains either a substance suitable to enhance anastomosis at that site, or another suitable drug. Once distal portion 92 of graft 66 is suitably located in vessel 16, inflatable balloon 80 is inserted into the interior of stent 72, as discussed above. Balloon 80 is then inflated to deploy stent 72 radially outwardly such that the outer diameter of distal portion 92 expands to a sufficient extent that it approximates the inner diameter of native vessel 16 and tightly fits therein.

Upon expansion of balloon 80, which is illustrated in FIG. 9B, the outer surface 98 of sheath 94 is preferably rendered discontinuous (or broken) to release the substance carried by intermediate region 100 of sheath 94. In one preferred embodiment, the substance contained by region 100 of sheath 94 includes an adhesive which immediately sets or cures with the passage of time once stent 72 is deployed in vessel 16. This enhances anchoring of distal portion 92 within vessel 16. Suitable adhesives are preferably bioadhesives such as fibrin glues commercially available under the tradenames Tisseel or Tissucol from Immuno, AG of Vienna, Austria; cyanacryolates commercially available under the tradenames Histoacryl, Bucrylate or Hexacryl; or Gelatin-Rocorcinol, formaldehyde, or mussel adhesive protein. In another preferred embodiment, growth factors or other biological substances are contained within sheath 94 which also enhance an anastomosis and healing in that region.

Figure 10:
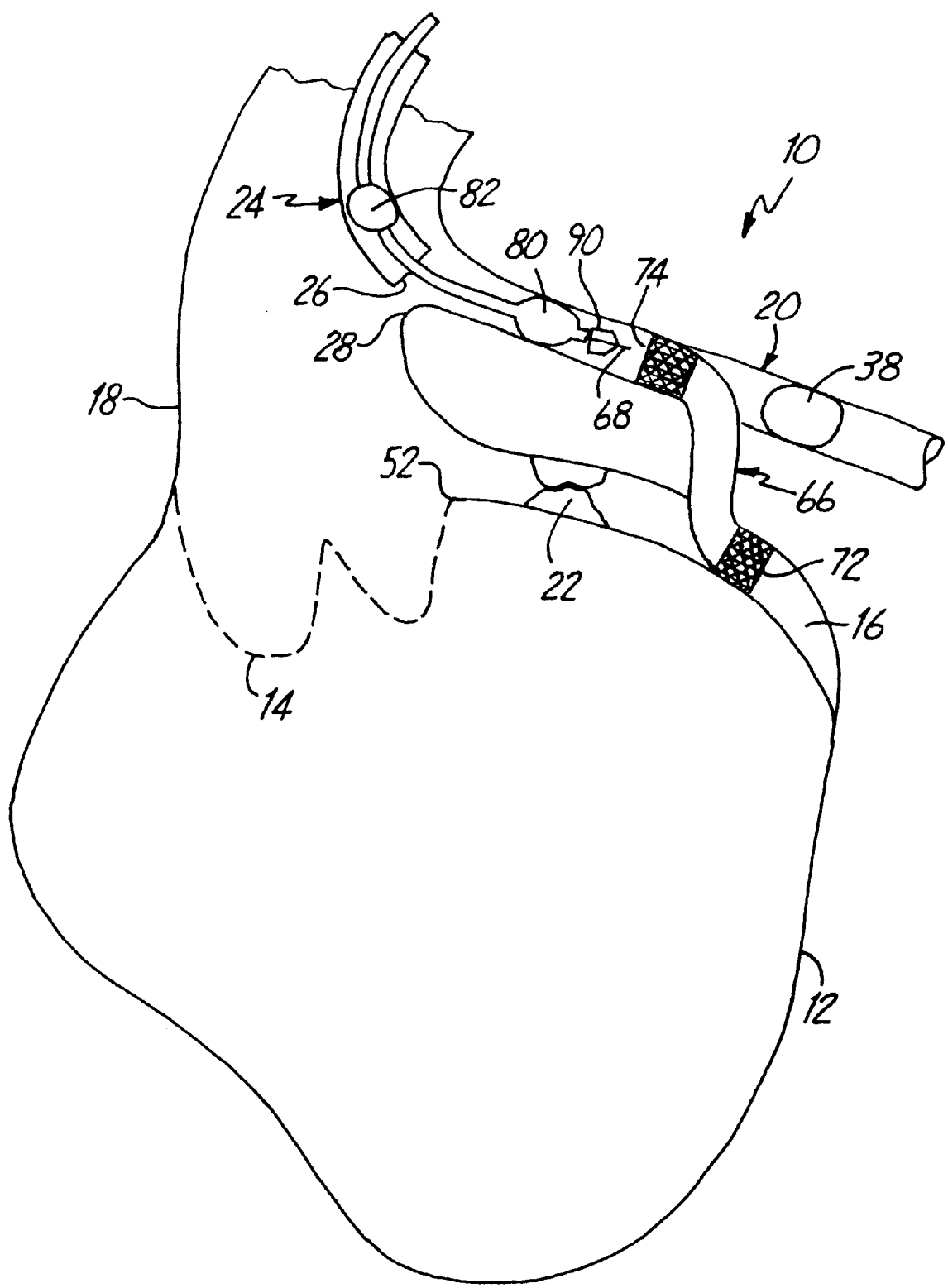
FIG. 10 illustrates a graft deployed as in FIGS. 9A and 9B between the branching vessel and the restricted parent vessel.

FIG. 10 illustrates a next step in performing a bypass in accordance with one aspect of the present invention. Once graft 66 is deployed, and the anastomosis sites have been formed in vessels 16 and 20, balloons 80 and 82 are removed. In addition, wire 68 and introducer 70 are also removed while stent 66 remains in place. Finally, guide catheter 24 is removed from the vascular system 10, and the procedure is completed.

Figure 11:
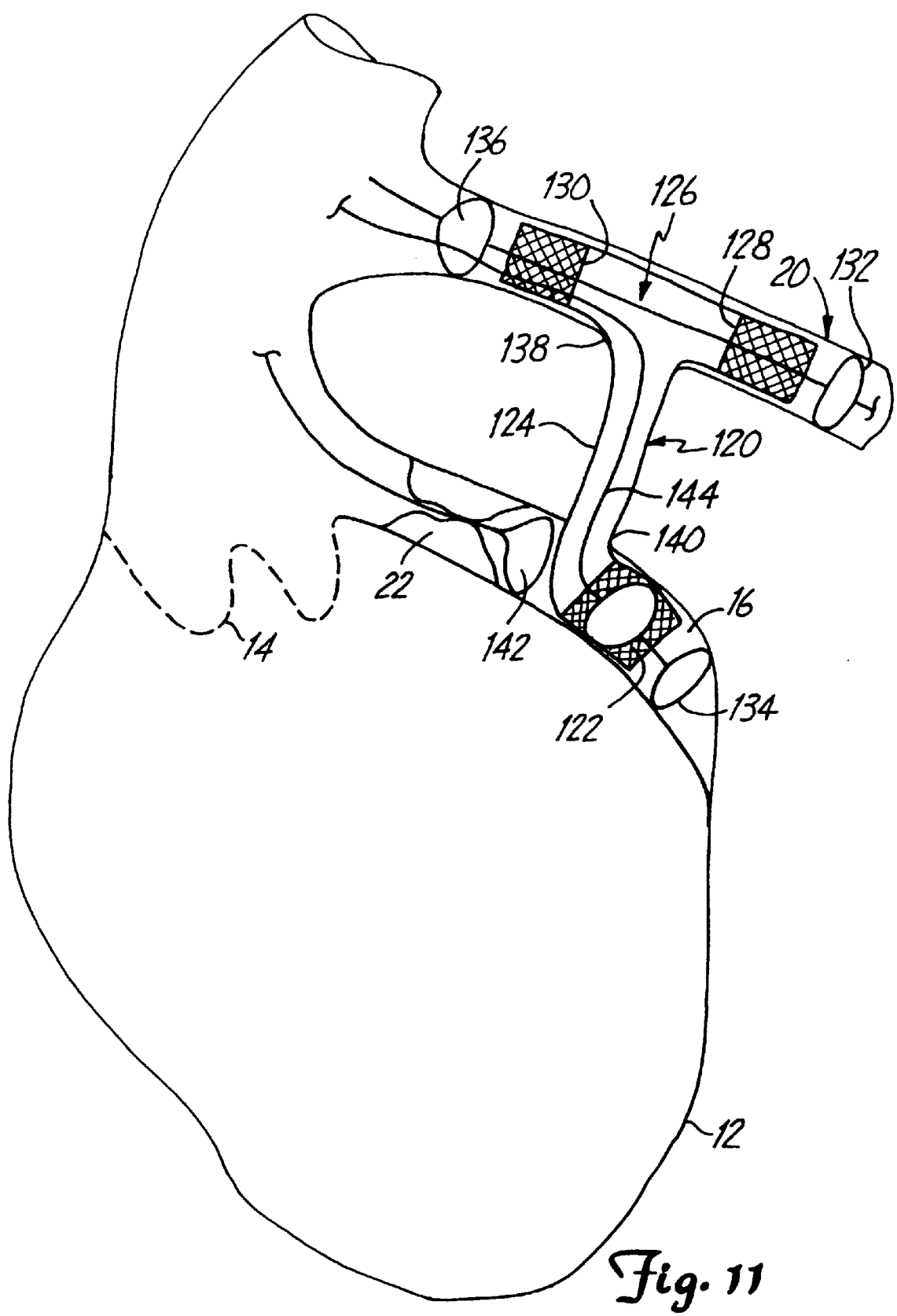
FIGS. 11 and 12 illustrate other embodiments of the present invention employing a bifurcated stent graft.
Figure 12:
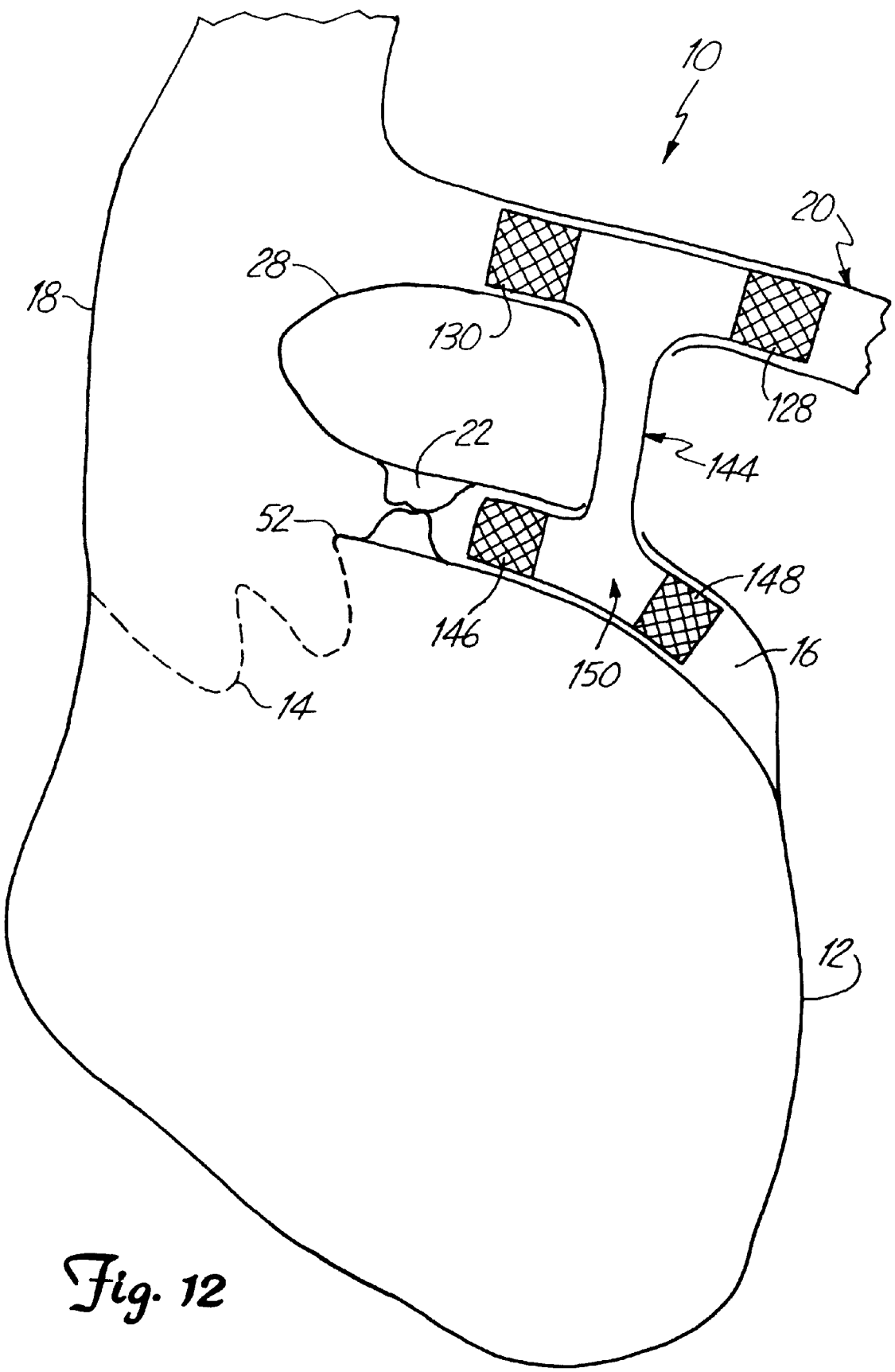

FIGS. 11 and 12 illustrate additional embodiments in accordance with the present invention. FIG. 11 illustrates the use of proximal bifurcated stent graft 120. Proximal bifurcated stent graft is similar to graft 66 in that it has a distal stent 122 coupled to a distal end of graft section 124. However, stent graft 120 also has a proximal end 126 which provides a bifurcated lumen having a pair of stents 128 and 130 attached to the bifurcated lumen portions of end 126. In the preferred embodiment, a pair of distal occlusion balloons 132 and 134 are provided in vessels 16 and 20, respectively. Also, a proximal occlusion balloon 136 is provided in vessel 20, or in another appropriate vessel proximal of the site at which the aperture 138 is formed in vessel 20. Occlusion balloon 142 is then inserted in vessel 16 and used to completely occlude vessel 16, if necessary. Once aperture 138 is formed, an aperture 140 is formed in vessel 16 in accordance with the methods described above, or similar methods. Guidewire 144 is advanced through aperture 140 and distal occlusion balloon 134 is inflated to occlude vessel 16 distal of aperture 140. A stent expansion balloon is then positioned in stent 122 and used to expand stent 122 as described above. Additional stent expansion balloons (or a single balloon) are then inserted within stents 128 and 130 and used to expand those stents to secure them within vessel 20. The occlusion balloons, and stent expansion balloons, along with the associated wires or other devices supporting those balloons, are then removed from the system and stent graft 120 remains in place.

FIG. 12 illustrates a stent graft 144 which is similar to stent graft 120, and is employed in a similar manner. However, stent graft 144 is a doubly bifurcated stent graft which not only includes balloons 128 and 130 in a bifurcated proximal tubular end 126, but stent graft 144 also includes stents 146 and 148 which form a distally bifurcated end 150. All four stents 128, 130, 146 and 148 are used to anchor stent graft 144 in place.

It has also been found that some grafts tend to degenerate after approximately 10 years of use. Therefore, in accordance with one additional aspect of the present invention, the grafts are structurally reinforced with a mechanical outer shell to strengthen the graft. In one embodiment, the mechanical outer shell is a sheath which is formed of, for example, woven Dacron, Gortex, or polyester. The sheath is preferably configured so that the vein graft can be passed through the sheath prior to deployment of the graft in the vasculature. Then, the reinforcing sheath is pulled at its opposite ends, in longitudinally opposing directions. This causes the woven sheath to tighten down around the outer surface of the vein graft and thereby reinforce the vein graft.

In another embodiment, the vein graft is wrapped with a material which strengthens the vein graft. In one embodiment, the vein graft is wrapped with, for example, hook and loop tape (such as Velcro tape) wherein the hooks on the hook and loop tape engage the adventitious layer of the vein graft. The hook and loop tape can be any suitable fabric backed microhoop strip which has hooks suitable for engaging the adventitious layer on the exterior of the vessel wall. Ultrasound is preferably used to measure the size of the vein and to adjust the tension in the reinforcement layer such that the interior of the reinforcement layer closely approximates the exterior dimension of the vein graft.

It should also be noted that, in one preferred embodiment, extra working space can be created in the chest cavity in order to facilitate manipulation of the various devices described herein. According to one aspect of the present invention, a needle or cutting tip catheter is used to form an incision in the branching vessel, as described above. Then, one of a number of things is used to create additional working space. For instance, a balloon may preferably be advanced through the hole in the branching vessel, expanded in the interstitial spaces proximate thereto to create additional working space. Also, a bioabsorbable, or removable, material can be optionally injected through the aperture in the branching vessel to expand the area thereabout and create additional working space. These features are preferably used in order to replace $CO_2$ injection which is commonly used in, for instance, laproscopic surgery.

Thus, it can be seen that the present invention involves a system by which coronary artery bypass procedures can be executed substantially percutaneously and transluminally. This serves to significantly reduce the disadvantages associated with prior treatment techniques. In the embodiment in which a branching vessel is used to form the conduit providing blood flow, as opposed to a graft, the present invention eliminates half of the intraluminal connections required in a typical graft procedure. In other words, since the branching vessel is only severed in one place, only one end of the branching vessel needs to be connected to the parent vessel. This requires only one intraluminal connection (or anastomosis) as opposed to two which are required where an anastomosis must be formed between a graft and both the conduit supplying the blood flow, and the artery receiving the blood flow. Further, since the present invention utilizes a branching vessel, it is relatively easy to occlude blood flow in the relevant vasculature (i.e., in the branching vasculature and the occluded vasculature). This occlusion is relatively easy as opposed to the necessity of occluding blood flow throughout the entire aorta in systems which provide a graft directly from the aorta.

Although the present invention has been described with reference to preferred embodiments, workers skilled in the art will recognize that changes may be made in form and detail without departing from the spirit and scope of the invention.

What is claimed is:

1. A method of percutaneously bypassing an incomplete occlusion in a restricted artery of a mammal having an aorta and a branching vessel branching from the aorta, the method comprising:

intraluminally accessing a first site in the branching vessel;

intraluminally forming an aperture in the branching vessel at the first site;

intraluminally forming a total occlusion in the restricted artery;

forming an aperture in the restricted artery distal of both the incomplete occlusion and the total occlusion; and providing a conduit to form a lumen communicating through the aperture in the branching vessel with a lumen in the branching vessel proximal of the first site and through the aperture in the restricted artery with a lumen of the restricted artery distal of the incomplete occlusion and the total occlusion.

2. The method of claim 1 wherein intraluminally forming an aperture in the branching vessel comprises:

intraluminally severing the branching vessel at the first site to form a severed end.

3. The method of claim 2 wherein providing a conduit comprises:

attaching a region of the branching vessel proximate the severed end to a region of the restricted artery proximate the aperture such that a lumen in the branching vessel communicates with a lumen in the restricted artery.

4. The method of claim 3 wherein attaching a region of the branching vessel comprises:

inserting the severed end of the branching vessel through the aperture in the restricted artery into the lumen of the restricted artery; and connecting the severed end to the restricted artery.

5. The method of claim 4 wherein connecting the severed end comprises:

deploying a stent in the restricted artery to attach the severed end to the restricted artery.

6. The method of claim 1 and further comprising:

prior to forming an aperture in the branching vessel, forming an occlusion in the branching vessel distal of the first site.

7. The method of claim 1 and further comprising:

prior to forming the aperture in the branching vessel, temporarily occluding the branching vessel proximal of a region in the branching vessel where the aperture is to be formed.

8. The method of claim 7 wherein temporarily occluding comprises:

advancing an expandable member through the branching vessel to the region proximal of the aperture in the branching vessel; and expanding the expandable member to occlude the branching vessel.

9. The method of claim 1 wherein providing a conduit comprises:

placing a first emitter in the region of the restricted artery distal of both the incomplete occlusion and the total occlusion and a second emitter in an end of the conduit, the first and second emitters emitting location signals;

sensing the location signals and providing an operator perceptible output indicative of the location of the end of the conduit relative to the region of the restricted artery distal of the incomplete occlusion and the total occlusion; and positioning the end of the conduit proximate a region of the restricted artery distal of the incomplete occlusion and the total occlusion based on the operator perceptible output.

10. A method of percutaneously bypassing a restriction in a restricted artery of a mammal having an aorta and a branching vessel branching from the aorta, the method comprising:

intraluminally accessing a first site in the branching vessel;

intraluminally severing the branching vessel at the first site to form a severed end;

forming an aperture in the restricted artery distal of the restriction; and attaching a region of the branching vessel proximate the severed end to a region of the restricted artery proximate the aperture such that a lumen in the branching vessel communicates with a lumen in the restricted artery.

11. The method of claim 10 wherein attaching a region of the branching vessel comprises:

inserting the severed end of the branching vessel through the aperture in the restricted artery into the lumen of the restricted artery; and connecting the severed end to the restricted artery.

12. The method of claim 11 wherein connecting the severed end comprises:

deploying a stent in the restricted artery to attach the severed end to the restricted artery.

13. The method of claim 10 wherein the restriction in the parent vessel is an incomplete occlusion, and further comprising:

prior to forming an aperture in the restricted artery, forming a total occlusion in the restricted artery proximal of a region where the aperture is to be formed.

14. The method of claim 10 wherein attaching a region of the branching vessel proximate the severed end comprises:

placing a first emitter in the region of the restricted artery distal of the restriction and a second emitter in the branching vessel proximate the severed end, the first and second emitters emitting location signals;

sensing the location signals and providing an operator perceptible output indicative of the location of the severed end relative to the region of the restricted artery distal of the restriction; and positioning the severed end proximate a region of the restricted artery distal of the restriction based on the operator perceptible output.

* * * * *